United States Patent [19]

Biermaier

[11] Patent Number: 5,314,668
[45] Date of Patent: May 24, 1994

[54] METHOD OF AUTOMATICALLY DISINFECTING DOOR HANDLES OF DISINFECTING UNITS

[76] Inventor: Stephan Biermaier, Ulrichstrasse 47, 8904 Friedberg 3, Fed. Rep. of Germany

[21] Appl. No.: 34,165

[22] Filed: Mar. 19, 1993

Related U.S. Application Data

[63] Continuation of Ser. No. 672,902, Mar. 21, 1991, abandoned.

[30] Foreign Application Priority Data

Mar. 23, 1990 [DE] Fed. Rep. of Germany ....... 4009454

[51] Int. Cl.[5] .............................. A61L 2/00; A61L 9/00
[52] U.S. Cl. ..................... 422/292; 422/301; 422/22; 422/27; 422/28; 134/104.1
[58] Field of Search ............... 422/292, 300, 301, 22, 422/36-28; 134/104.11

[56] References Cited

U.S. PATENT DOCUMENTS

| | | | |
|---|---|---|---|
| 3,314,746 | 4/1967 | Millar | 422/123 |
| 3,871,824 | 3/1975 | Rechtsteiner et al. | 21/58 |
| 4,046,508 | 9/1977 | McDonald | 21/77 |
| 4,658,469 | 4/1987 | Hawkins | 16/110 R |
| 4,736,416 | 4/1988 | Weinert | 422/28 |
| 4,783,321 | 11/1988 | Spence | 422/300 |

FOREIGN PATENT DOCUMENTS 2591115 12/1985 France .
568074 4/1974 Switzerland .

*Primary Examiner*—Lyle A. Alexander
*Attorney, Agent, or Firm*—Cushman, Darby & Cushman

[57] ABSTRACT

An automated method of disinfecting door handles of units such as disinfecting apparatus. Disinfecting occurs in response to a predetermined function or state, such as the termination of a cleansing operation in a disinfecting apparatus, established time intervals, or a set number of manipulations of the door handle. The door handle may be disinfected by physically moving the handle into the disinfecting apparatus chamber. Alternatively, the handle may be sprayed or impregnated with a disinfecting solution. As another alternative, the door handle may be covered with a sterile, protective film. As a final alternative, the door handle may be disinfected by thermal convection.

10 Claims, 7 Drawing Sheets

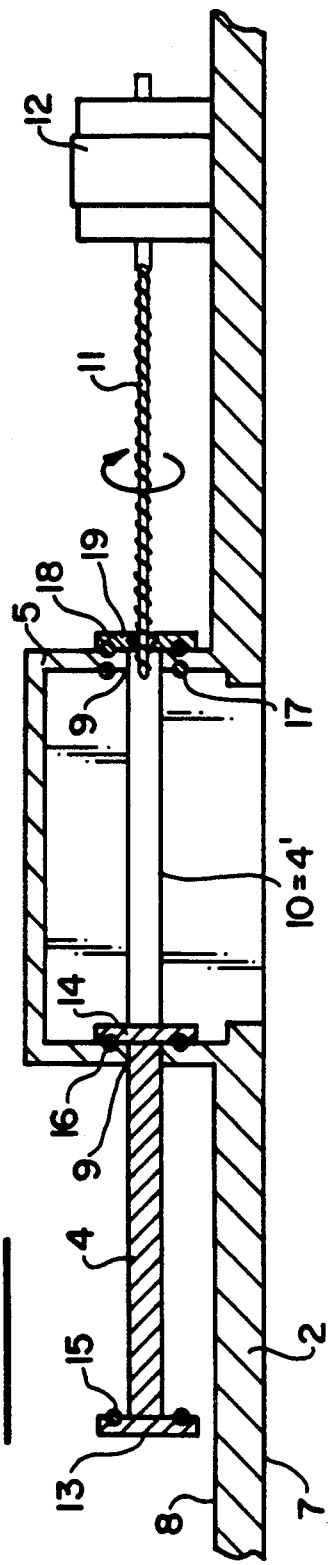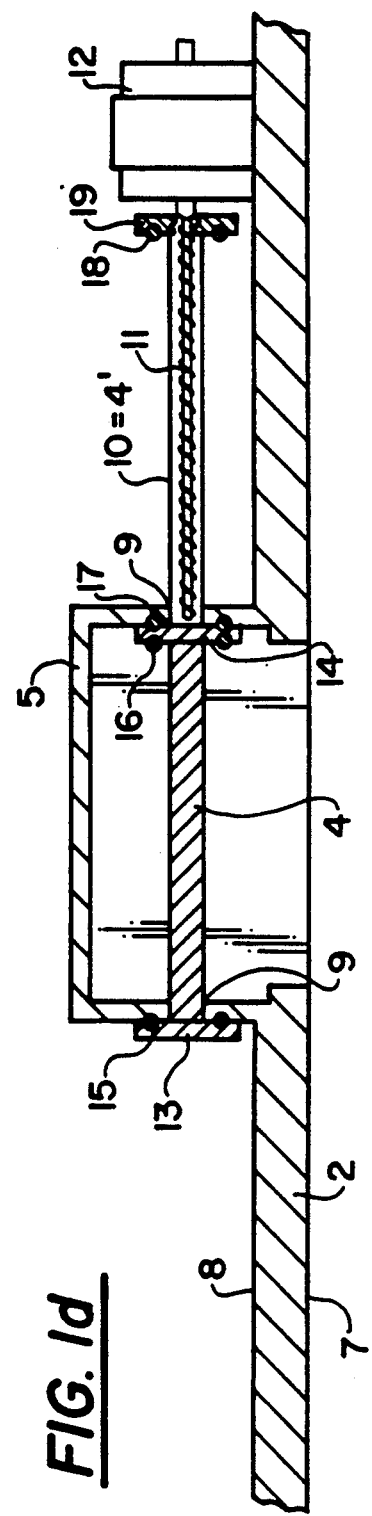

METHOD OF AUTOMATICALLY DISINFECTING DOOR HANDLES OF DISINFECTING UNITS

This is a continuation application Ser. No. 07/672,902, filed on Mar. 21, 1991, which was abandoned upon the filing hereof.

FIELD OF THE INVENTION

The instant invention relates to a means for disinfecting door handles, especially door handles of disinfecting apparatus.

BACKGROUND OF THE INVENTION

It has become apparent in hospitals, clinics, laboratories, doctor's offices, and the like that door handles are cleaned quite irregularly only and, therefore, present a constant source of contamination, germs, bacteria, and the like. Specifically, it was found that when loading disinfecting apparatus, washers, sterilizing equipment, and the like the handle of the apparatus becomes contaminated and on removal of the disinfected, asepticized, or sterilized articles germs are transmitted from the door handle by the hands of the user to the disinfected articles. To avoid such problems, so far the handle had to be decontaminated manually prior to each removal from the disinfecting apparatus and, as experience tells us, often that was not done. It is also known to overcome the above mentioned difficulty by providing a door without a handle and opening or closing it by levers which are foot-operated. Yet the corrresponding structures are expensive and they do not prevent the operator from touching, almost automatically, the outside of the door which usually is contaminated.

SUMMARY OF THE INVENTION

It is the object of the invention to provide a disinfecting means which will guarantee that, when needed, the door handle is disinfected prior to use.

That object is met, in accordance with the invention, in that means are provided which positively assure the automatic disinfection of the door handle in response to a higher-order function.

Advantageous modifications and further developments of the invention are recited in the subsidiary claims.

The invention thus makes sure that the door handle is rendered aseptic automatically, regardless of a user's manipulation.

In a first variant embodiment of the invention the door handle of a disinfecting apparatus is moved into the washer chamber during the cleansing operation so as to be disinfected and made aseptic together with the items or material to be cleaned in the apparatus. According to various subvariants of this principle either the door panel is turned over or the handle itself is moved into the washer chamber or the washer chamber is enlarged by movable members so that the door handle will be included in that space.

According to another variant of the invention the door handle is sprayed or impregnated with a disinfectant solution, independently of the operator.

A third basic embodiment of the invention provides for covering the door handle with a protective film which is being renewed automatically.

In accordance with yet another modification of the invention the handle is disinfected thermally.

It is assured with all these fundamental variants of the invention, as well as with other subvariants to be described below, that the handle is sufficiently well disinfected, regardless of any negligence on the part of the user.

BRIEF DESCRIPTION OF THE DRAWING

The invention will be described further, by way of example, with reference to the accompanying drawings, in which:

FIG. 1b is a cross sectional elevation of the door and handle along line A-B in FIG. 1a;

FIGS. 1c and 1d are further cross sections of the door and handle along line C-D in FIG. 1a, showing two different limit positions of the door handle;

DESCRIPTION OF THE PREFERRED EMBODIMENTS

Figure 1A:
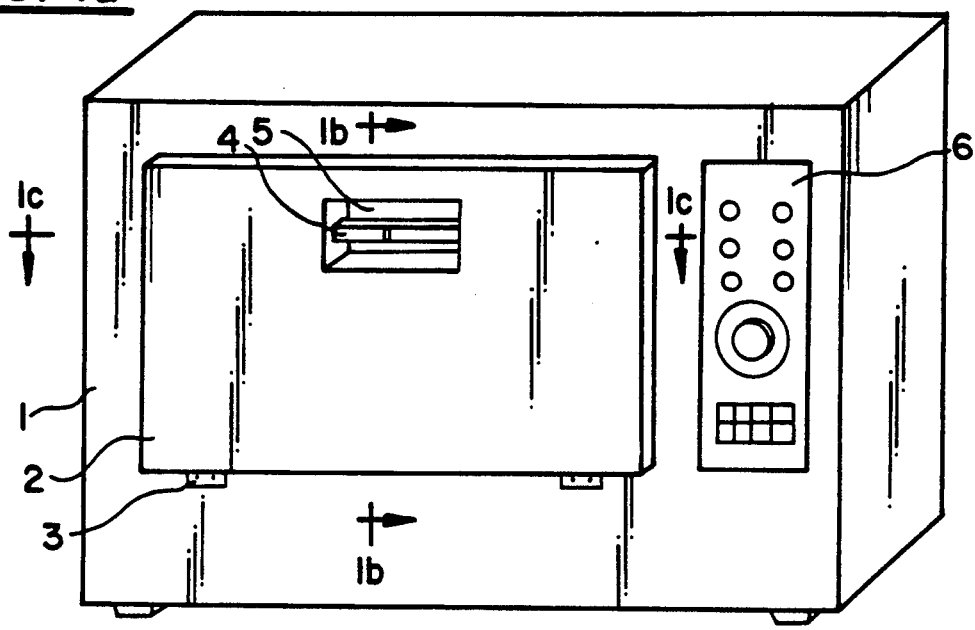
FIG. 1a is a diagrammatic perspective view of a disinfecting apparatus showing a first embodiment of a disinfecting means according to the invention.

FIG. 1a is a diagrammatic presentation of a disinfecting apparatus 1 comprising a door 2 secured to the housing of the apparatus by way of a hinge 3. In this instance a door handle 4 is formed like a tube to be grasped which extends lengthwise in a hollow 5 formed in the door 2.-. Various operating elements of the disinfecting apparatus 1 are designated generally by reference numeral 6.

Figure 1B:
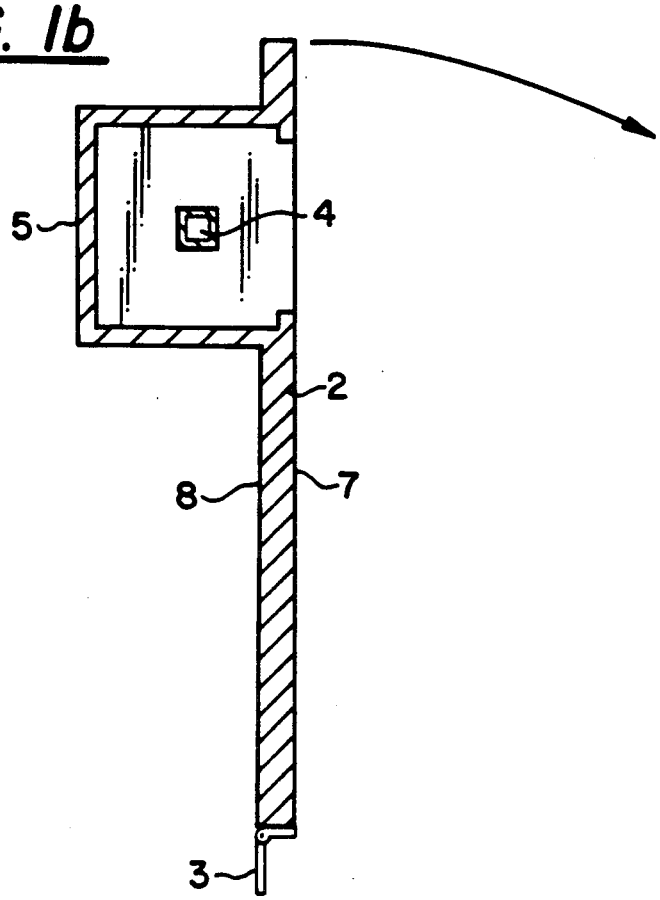

The arrangement of the hollow 5 associated with the door handle 4 and the handle itself are shown in greater detail in the cross sectional elevation of FIG. 1b. As will be seen, the hollow 5 is open toward the outer surface 7 of the door so that the handle 4 can be grasped from outside. The hollow 5 thus extends towards the inner surface 8 of the door.

As shown in FIGS. 1c and 1d, the hollow 5 has two side bores 9 which are mutually aligned and whose axis extends parallel to the plane of the door 2. The door handle 4 is displaceable through these bores 9 in the direction of its longitudinal axis so that it will be located inside the hollow 5 which is accessible from outside, when in its one limit position (FIG. 1d). In its other limit position (FIG. 1c), the door handle will be outside of the hollow 5, finding itself in the interior of the washer chamber of the disinfecting apparatus. In the latter limit position it will be cleansed and disinfected together with the items to be washed.

Specifically, a tubular extension 10 formed with an internal thread is mounted at one end of the door handle 4, and a spindle 11 driven by an electric motor 12 engages said thread. The door handle 4 is shifted between the two end positions illustrated when the motor 12 rotates the spindle 11.

The extension 10 of the door handle also may be used as part of the overall handle (part 4'). In that event either part 4 or part 4' will find itself alternatingly in the hollow and inside the washer chamber. The corresponding control may be devised so that the part last disinfected is moved into the hollow after each cleansing operation.

The bores 9 may be sealed in various ways with respect to the washer chamber of the disinfecting apparatus. In a variant embodiment, not shown, sealing rings may be positioned in the bores 9. In the embodiment shown, the door handle 4 has two end flanges 13 and 14 on which sealing rings 15 and 16, respectively, are mounted. One of the end flanges 14 is located within the hollow 5, while the other one 13 always remains in the washer chamber. The free end of the extension 10 of the handle is formed with another end flange 19 including a sealing ring 18 which faces the hollow 5. Of course, any known kind of sealing means can be used here and it should be noted that seals will be sufficient, in disinfecting apparatus, if they are splash proof since the interior of the customary disinfecting machines never is pressurized with respect to the surroundings.

The motor 12 is controlled by the program controller (not shown) of the disinfecting apparatus, for instance in a manner that will move the door handle 4 into the washer chamber at the beginning of the cleansing cycle (FIG. 1c) and will return it into the hollow 5 when the cleansing and possibly also a drying cycle are completed. In this manner it is assured that the door handle positively is disinfected automatically during each disinfecting operation.

In the embodiment shown (cf. especially FIG. 1b) the door handle 4 is of square cross section as this will prevent the handle from being rotated about its own axis so that it could no longer be shifted.

In accordance with another modification, not shown, the motor 11 and spindle 12 could be replaced by an electromagnet whose armature could be the extension 10 of the handle. It is also conceivable to use a gear instead of the spindle 12 and have it mesh with teeth on the outer surface of the extension of the handle. In other words, the extension of the handle would be a rack.

In another modified embodiment, not illustrated, the door handle 4 is moved into the position shown in FIG. 1c by means of linkages, ropes and pulleys and the like upon closing of the door, an operation which, at the same time, tensions a spring which, however, is locked in the terminal position illustrated in FIG. 1c. Upon completing a cleansing operation the locking may be released by an electromagnet on command from the controller so that the spring then can move the door handle back into the other end position shown in FIG. 1d.

A second embodiment of the invention is presented in FIGS. 2a to 2d. In that case the door handle is stationary and the hollow is formed by a movable flap which permits access to the handle from outside, in its one limit position, and from the inside of the washer chamber in its other limit position.

Figure 2A:
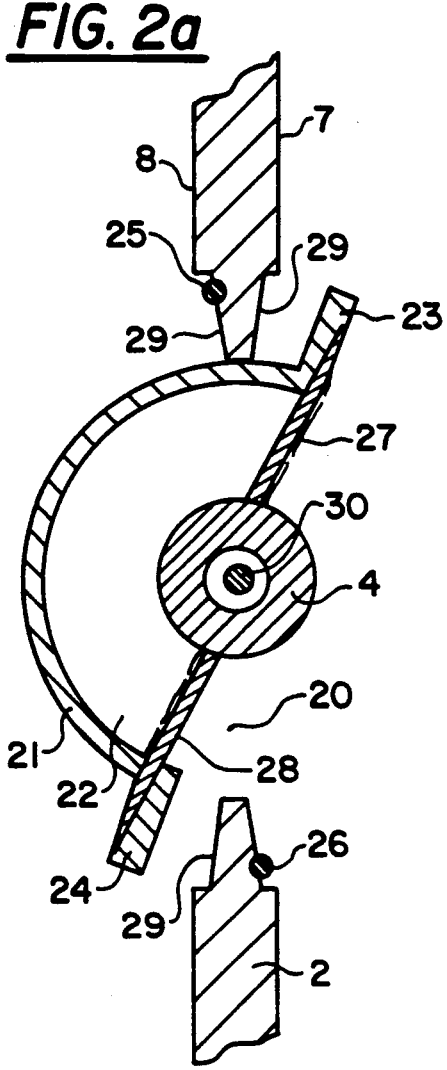
FIGS. 2a and 2c are cross sectional elevations of the door and handle of a disinfecting apparatus according to a second embodiment of the invention, showing two different limit positions.

More particularly, the door 2 is formed with a window 20 in the area of the door handle 4. A semicylindrical flap 21 having sidewalls 22 is inserted in the window in such manner that the inside of the flap at the same time presents the hollow 5. The flap is pivotable between two limit positions. In FIGS. 2a and 2b the flap 21 is shown in the limit position in which the door handle 4 is accessible from the outer surface 7 of the door. In the other limit position according to FIGS. 2c and 2d, on the other hand, the flap 21 closes the window 20 towards the outside 7, whereby the handle 4 is exposed towards the washer chamber and included in the disinfecting procedure.

The semicylindrical flap 21 is formed with paraxial webs 23 and 24 projecting radially outwardly and serving sealing purposes as well as to stop and define at least one of the limit positions (FIG. 2c). These webs extend for the full length of the cylinder and enter into engagement with paraxial seals 25 and 26, respectively, when the flap adopts the limit position shown in FIGS. 2c and 2d. The end walls 22 are formed with webs 27 and 28 which extend substantially radially in the plane of the respective webs 23, 24 and carry sealing strips. In the area of engagement of the webs 23 and 24, the door is formed with tapered portions 29 whose surfaces are aligned with the axis of rotation so that the webs will enter into planar engagement thereby assuring perfect abutment of the webs 23 and 24 against the door.

Figure 2:
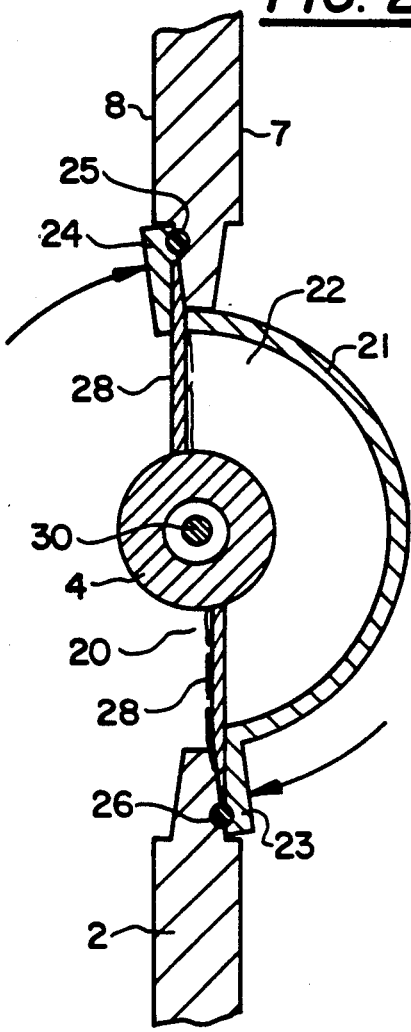
FIGS. 2b and 2d are perspective presentations of the outer face of the door in the two limit positions illustrated in FIGS. 2a and 2c.
Figure 2B:
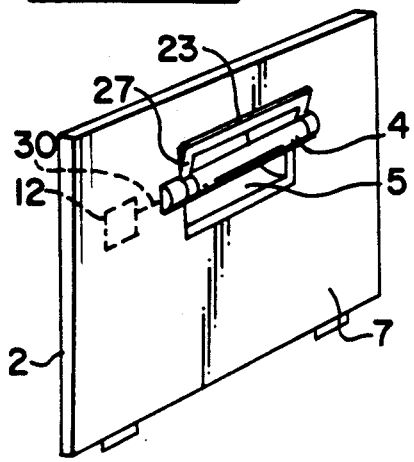
Figure 2D:
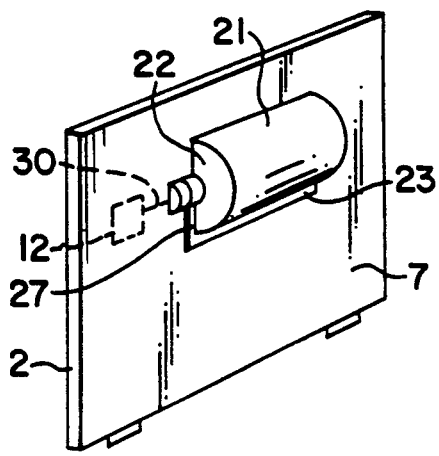

As indicated in FIGS. 2b and 2d, the flap 21 is driven by a motor 12 and a shaft 30. Here, too, the motor is controlled by the central controller of the disinfecting apparatus so that it is assured that the flap will be in the position illustrated in FIGS. 2c and 2d during each cleansing operation, whereby the door handle is disinfected. Upon completion of the washing cycle the flap is "opened" once more so that the door handle 4 becomes accessible from outside.

The seals used in the embodiment of FIGS. 2a to 2d may be replaced by other known sealing means, such as rubber lips which extend all around the square window 20 and make sure the seal is splash proof. Once again the motor 30 may be replaced by an electromagnet which actuates the flap through links. It is also possible to provide for mechanical actuation of the flap through the closing of the door, as explained with reference to FIG. 1.

Figure 3A:
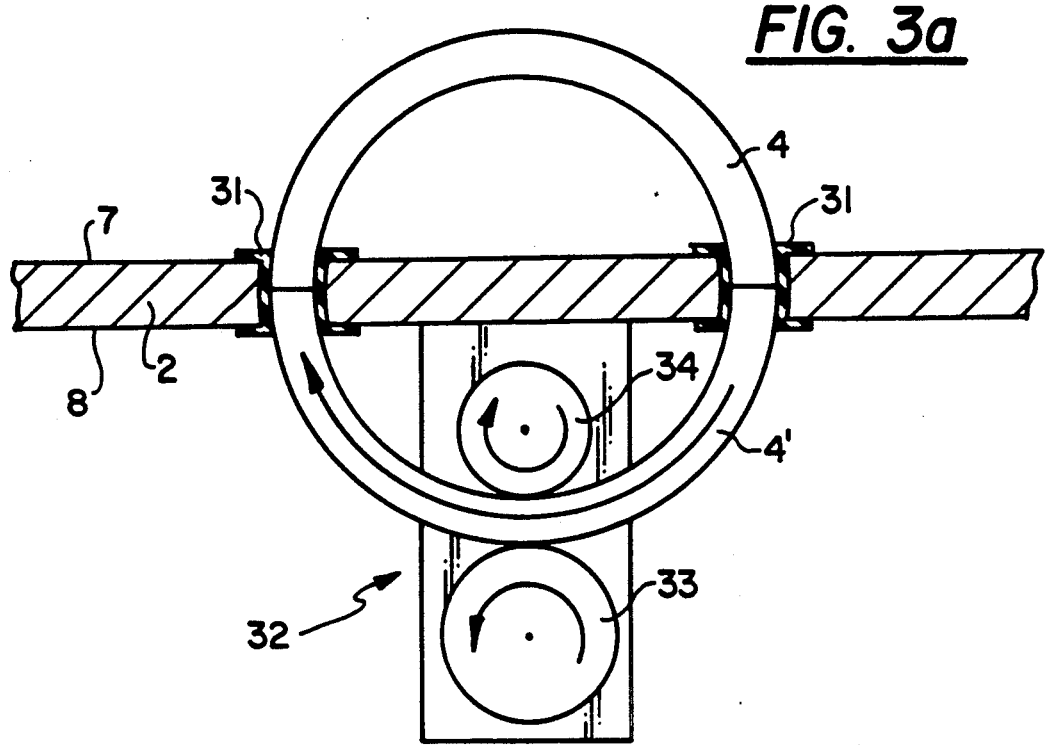
FIG. 3a is a cross sectional elevation of a door and door handle of a disinfecting apparatus according to a third embodiment of the invention, including a door handle which is movable with respect to the door.
Figure 3B:
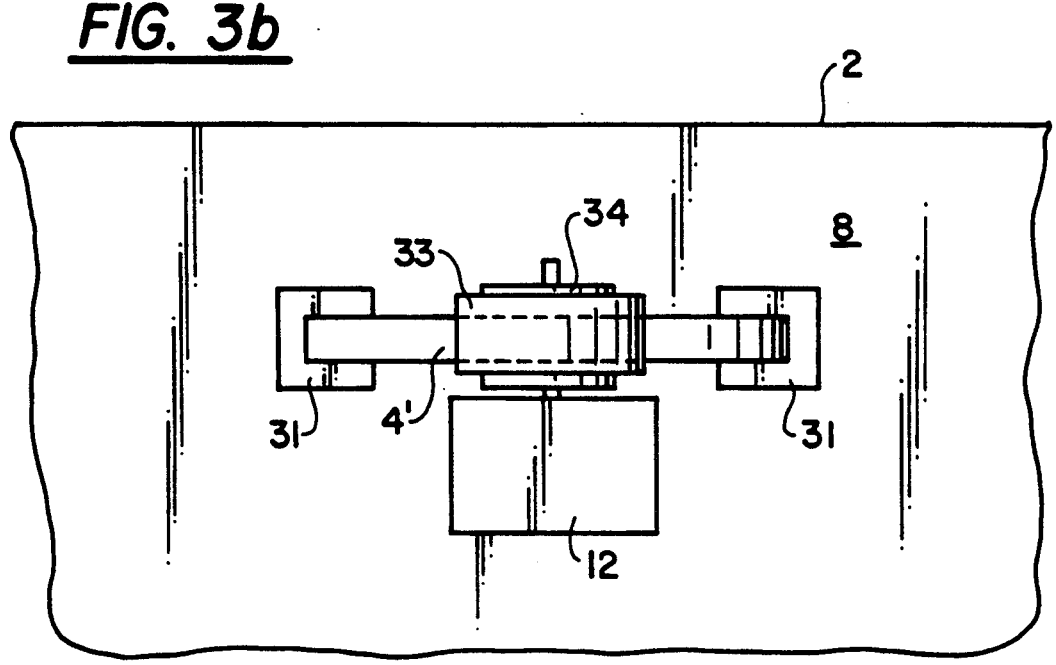
FIG. 3b illustrates the inner face of the door of the embodiment shown in FIG. 3a FIG. 4 is a perspective view, looking at the inside surface of the door of a disinfecting apparatus according to a fourth embodiment of the invention, comprising a movable flap to open or close a window through which the door handle may be reached.

FIGS. 3a and 3b present a third embodiment of the invention having a door handle 4 in the form of a closed ring which is inserted in two sealed (seals 31) apertures in the door 2 in such manner that one part 4 is located at the outer surface 7 and another part 4' at the inner surface 8 of the door 2. A drive mechanism 32 consisting of an electric motor 12 comprising a drive roller 33 and a contact pressure roller 34 rotates the door handle in response to the controller of the disinfecting apparatus such that the part of the door handle 4 inside the washer chamber during the disinfection process is subjected to disinfection and, upon completion thereof, is again moved to the outside. The ring of the door handle 4 is given a square cross section to facilitate its transportation as the drive roller 33 and the contact pressure roller 34 thus meet with a sufficiently large friction surface.

Figure 4:
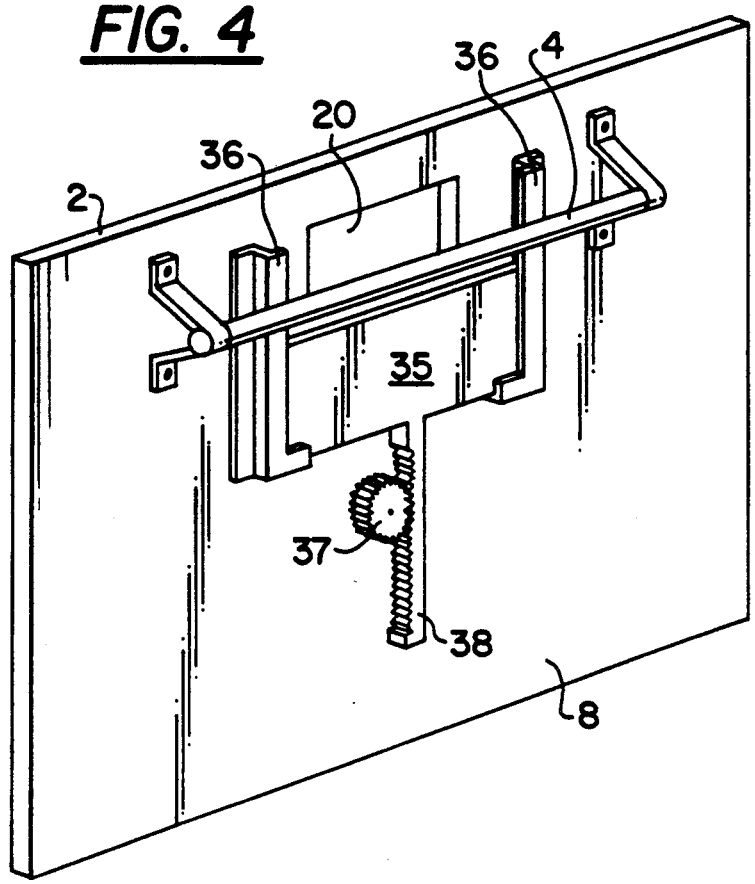

FIG. 4 shows a fourth embodiment of the invention with which the door handle 4 is secured firmly at the inner surface 8 of the door 2 and accessible from outside through a window 20 formed in the door. The window is opened and closed by a movable flap 35. In the embodiment shown, the flap is guided in sectional guide means 36 mounted at the inner surface 8 of the door 2 and reciprocated by an electric motor (not shown), a pinion 37 and a rack 38 connected to the flap 35 and meshing with the pinion 37. In this case, too, the motor is controlled by the controller of the disinfecting apparatus in such a way that the window 20 will be closed during the cleansing process. Of course, seals are provided between the flap 35 and the circumference of the window 20. Modifications of the drive means of the flap 35 may be provided similar to those explained with reference to the other embodiments.

Figure 5:
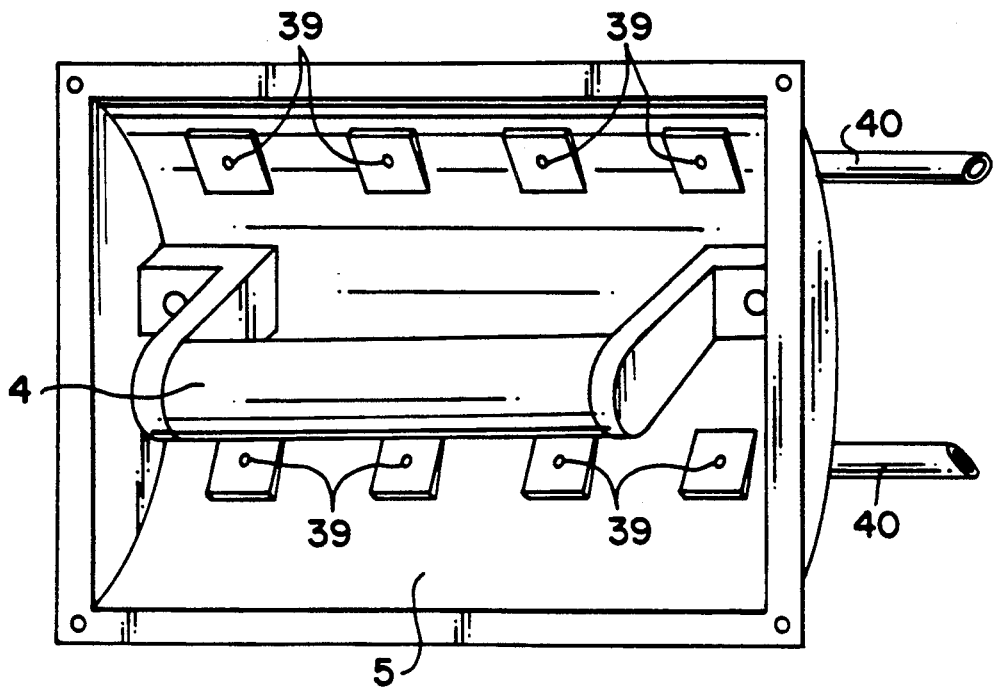
FIG. 5 illustrates a door handle and an associated hollow as well as spray nozzles of a disinfecting apparatus according to a fifth embodiment of the invention.

FIG. 5 illustrates a fifth embodiment of the invention with which the door handle 4 is disposed in the hollow 5 in which there are a number of spray nozzles 39 which are directed towards the door handle 4 and communicate with a source of liquid disinfectant through a plurality of hoses or tubes 40. Conveying means, not shown, for the disinfecting solution, such as a feed pump, a pressure fluid source in combination with a magnetic valve, and the like under the control of the controller of the disinfecting apparatus make sure that disinfectant is sprayed on the door handle 4 at predetermined times, for instance whenever a cleansing operation is finished.

Figure 6:
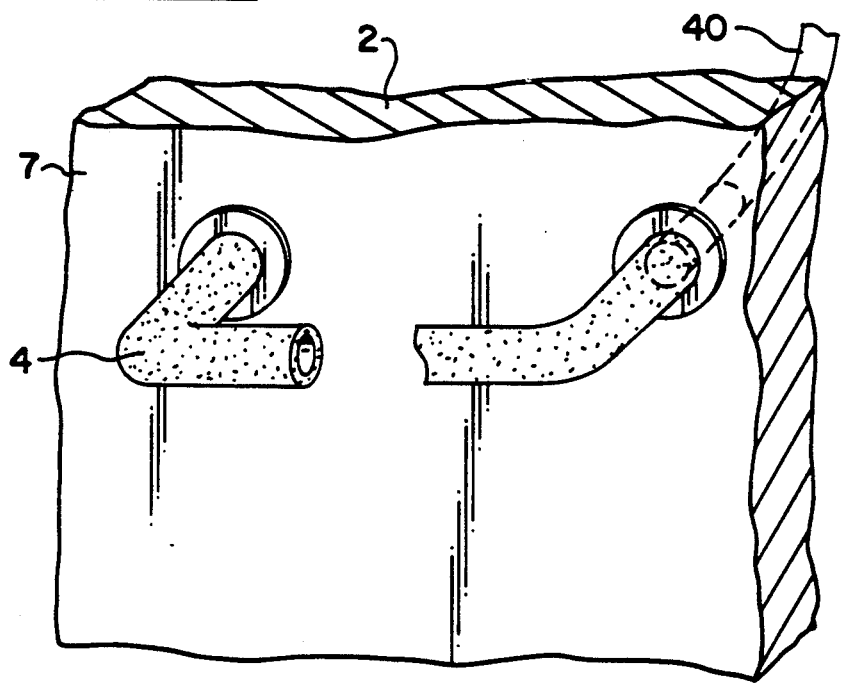
FIG. 6 shows part of the door and door handle of a disinfecting apparatus according to a sixth embodiment of the invention.

A sixth embodiment of the invention is shown in FIG. 6. Here the door handle 4 is made of porous material, such as sintered metal, and it is connected through a hose or tube 40 to a source of liquid disinfectant. Under the control of the control unit of the disinfecting apparatus the door handle 4 is impregnated with disinfecting solution from its interior, and it stores the solution in its pores. In the embodiment shown, the door handle 4 is embodied by a hollow tube of porous material. That affords the most uniform impregnation of the door handle with disinfectant. Once more it is advantageous to admit fresh disinfecting solution to the door handle during predetermined phases of the cleansing process.

Figure 7:
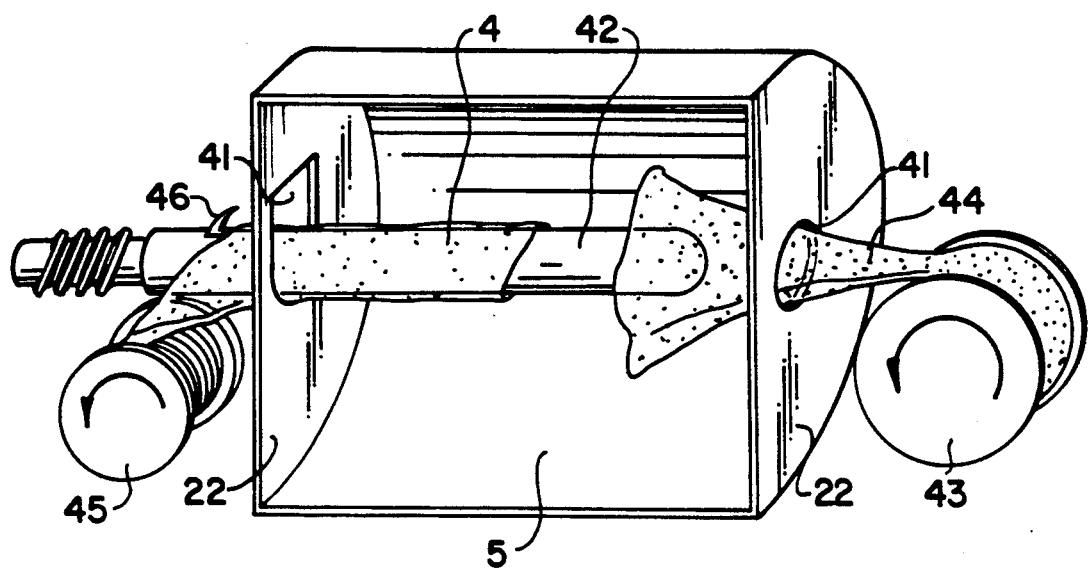
FIG. 7 illustrates a door handle and an associated hollow of a disinfecting apparatus according to a seventh embodiment of the invention

FIG. 7 shows a seventh embodiment of the invention with which the door handle is sterile by virtue of the fact that its surface consists of sterile film material which is renewed automatically. Once more, the door handle is arranged in a hollow 5 having mutually aligned apertures 41 in its sidewalls 22 to receive a support member 42 of the handle 4. A supply reel 43 of tubular film material 44 to be pulled over the support member 42 to form the door handle 4 together with the support member is disposed next to the hollow 5. At the other side of the hollow there is a discharge reel 45 on which the used sections of the tubular film material 44 are wound for removal. A radially projecting knife 46 which slits open the tubular film material is provided at the discharge end of the support member 42 to separate the tubular film material 44 from the support member.

The discharge reel 45 is driven by a motor, not shown, in the direction of the arrow at such intervals as are determined by the controller of the disinfecting apparatus. In this manner the sections of the tubular film material 44 located in the hollow are renewed in the given intervals. The support member 42 may be displaced in longitudinal direction so that a new tubular film may be slipped on the free end of the support member which is thus exposed for receipt of said hose of film. Preferably, the control unit of the disinfecting apparatus drives the motor to advance the discharge reel 45 whenever a cleansing process is completed. Hereby fresh film always is available in the range of the door handle for the subsequent withdrawal from the disinfecting apparatus.

Figure 8:
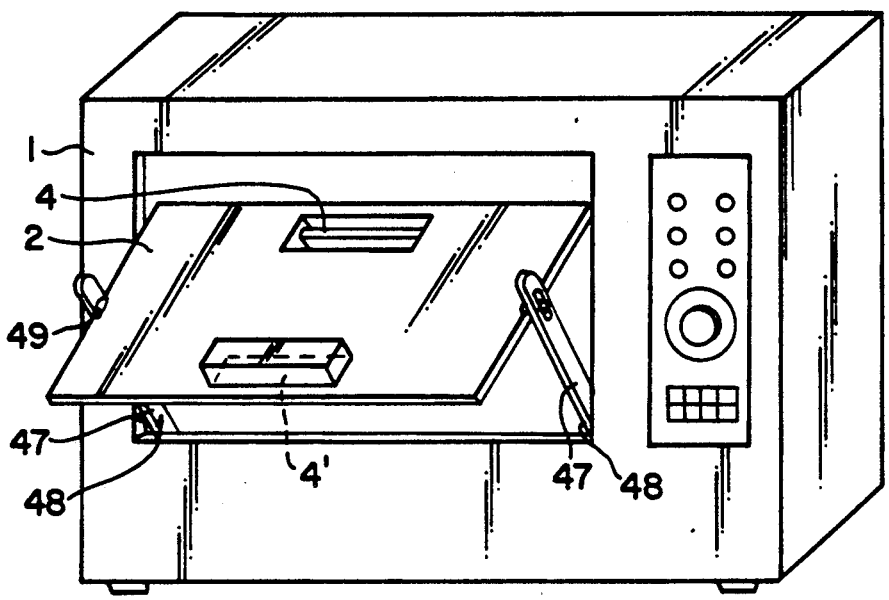
FIG. 8 is a diagrammatic perspective view of the front of a disinfecting apparatus comprising a door supported for reversal in accordance with an eighth embodiment of the invention.

FIG. 8 illustrates another embodiment of the invention. In this case the door 2 is provided on either side with a handle 4 and 4' supported for "reversal" in double hinges so that either door surface and thus either door handle will alternatingly face the washer chamber. In the particular embodiment illustrated, the door 2 is rotatably supported in two hinge links 47 one end each of which is secured in pivot bearings 48 at the housing of the disinfecting apparatus 1. At the other end of the hinge links 47 there is a pivot bearing 49 to permit turning of the door. The pivot bearing 49 preferably is of such design that it allows the door 2 to be rotated only in one direction. That can be accomplished by ratched pawls for example. And it makes sure that following each opening, the door can be closed only if rotated through 180°. In this manner the door handles 4 and 4' positively are disinfected alternatingly, each during every other cleansing operation.

Figure 9:
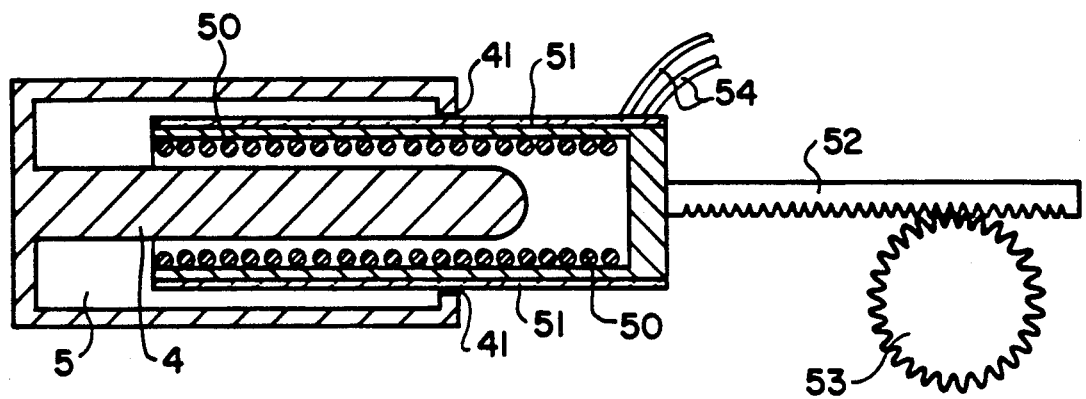
FIG. 9 illustrates a door handle and an associated hollow comprising an induction coil for heating and thus disinfecting the door handle according to a ninth embodiment of the invention.

FIG. 9 shows a ninth embodiment of the invention with which the door handle 4 is sterilized thermally. In this case the door handle 4 is fixed at one end in the hollow 5, its free end projecting through an aperture 41 out of the hollow 5. For disinfecting purposes, an induction coil 50 can be moved temporarily over the door handle 4 to heat the surface of the handle to a temperature at which all the germs present will be killed. If the induction coil 50 is supplied with high frequency current the skin effect will cause only the upper boundary layer of the door handle 4 to become heated, and that is sufficient for sterilizing or disinfecting it. It also has the effect that the door handle will cool down very quickly and thus be ready for renewed use. The induction coil 50 is furnished with a thermally insulating coating 51 to prevent burns. The control unit of the disinfecting apparatus controls the induction coil 50 so that it will move into operating position at predetermined times of the cleansing cycle, preferably towards the end thereof. To accomplish that, the induction coil 50 is connected to a rack 52 meshing with a pinion 53 which is driven by a motor. Flexible connecting wires 54 are connected to a high frequency generator. As an additional safety measure, the induction coil 50 remains in operative position upon switchoff of the exciter current until the door handle 4 has cooled down to a temperature at which the risk of burns definitely is excluded.

Although the embodiments of the invention were described above with reference to a disinfection apparatus it should be noted that at least some of the embodiments are suitable also for disinfecting other kinds of door handles, such as handles of cabinets for the sterile storing of surgical instruments, doors of operating theaters or rooms in hospitals etc.

In certain instances, such as with room doors and the like, the invention provides for rendering the disinfecting means effective at certain given intervals in time, for example by a time switch, clock control, and the like. According to another modification of the invention the disinfection means may be made operative in response to manipulation of the door handle, such as after each individual manipulation or following a given series of such manipulations. In the latter case there will be a counter to initiate the disinfection whenever a predetermined count is reached. Such cases just cited are all examples of a controlling program. It is this program that is responsible for automating the disinfecting methods disclosed earlier, by activating the handle sterilization process when a predetermined state or function is sensed.

An additional advantage of the embodiments shown in FIGS. 2, 5, and 8 is to be seen in the fact that the hollow of the door handle which likewise is subject to contamination by germs is included in the disinfecting procedure. In the case of FIG. 8 even the entire outer surface of the door is disinfected.

What is claimed is:

1. A disinfecting system comprising:
    a disinfecting apparatus comprising wall means defining a disinfection chamber, a door for providing selective access to said disinfection chamber, means for disinfecting objects placed within said chamber, and a handle mounted to one of said wall means and said door and accessible from an exterior of said disinfecting apparatus;
    wherein an improvement comprises:
        handle disinfecting means for selectively, automatically disinfecting said handle while said handle remains mounted to said one of said wall means and said door, said handle disinfecting means including a source of liquid disinfectant, at least one spray nozzle provided on at least one of said door and said wall means, and separate from said handle, mounted upon the exterior of said disinfecting apparatus and for directing a liquid disinfectant toward and onto a surface of the handle, and means for conveying liquid disinfectant from said source to said at least one spray nozzle; and
        control means for controlling an operation of said handle disinfecting means, so that said liquid disinfectant is conveyed to said handle disinfecting means one of at predetermined time intervals and in response to the disinfecting apparatus entering a specified state.

2. A disinfecting system comprising:
    a disinfecting apparatus having a disinfecting means for disinfecting objects placed within an interior of the apparatus; and
    a handle attached to and accessible from an exterior of said disinfecting apparatus;
    wherein an improvement comprises:
    means for drawing sterile tubular film over said handle including:
        a supply reel located at a first end of said handle to supply the film to enclose said handle;
        a discharge reel disposed at a second end of said handle to take up the film from the handle;
        a knife, disposed adjacent to said discharge reel, for cutting the film after passing over said handle and before being wound on said discharge reel; and
        rotating means for rotating said reels so as to transport the film over said handle; and wherein said system further comprises:
        control means for controlling an operation of said drawing means, for automatically enclosing the handle within said sterile tubular film in response to one of passage of a predetermined period of time and a predetermined state of operation of the disinfecting apparatus.

3. A disinfecting system comprising:
    a disinfecting apparatus comprising wall means defining a disinfection chamber, a door for providing selective access to said disinfection chamber, means for disinfecting objects placed within said chamber, and a handle mounted to one of said wall means and said door and accessible from an exterior of said disinfecting apparatus;
    wherein an improvement comprises:
        handle disinfecting means for selectively, automatically disinfecting said handle while said handle remains mounted to said one of said wall means and said door, said handle disinfecting means including an induction coil mounted to one of said wall means and said door and adjacent to handle so as to direct a magnetic field produced by said coil about said handle; and
        control means for controlling an operation of said handle disinfecting means so that said induction coil is selectively moved in and out of an operating position on the basis of a predetermined cleaning cycle of said disinfecting apparatus.

4. A disinfecting system according to claim 3, wherein said handle disinfection means includes means for transporting said induction coil to surround said handle in a first position and to withdraw from said handle in a second position.

5. A disinfecting system comprising:
    a disinfecting apparatus comprising wall means defining a disinfection chamber, a door for providing selective access to said disinfection chamber, means for disinfecting objects placed within the chamber, and a handle fixedly mounted to one of said wall means and said door so as to be at least selectively accessible from an exterior of said disinfecting apparatus;
    wherein an improvement comprises:
        handle disinfecting means for selectively, automatically disinfecting said handle while said handle remains mounted to said one of said wall means and said door, said handle disinfecting means including means for selectively exposing said handle to an interior of said chamber while said disinfecting apparatus is operating, said handle disinfecting means providing access to the handle form outside said chamber when in a first state and providing access to the handle from inside said chamber when in a second state, wherein in said second state the handle can be disinfected together with the objects in said chamber; and
        control means for controlling an operation of said handle disinfecting means, said control means placing the handle disinfecting means in one of said first and second states on the basis of a predetermined cleaning cycle of the disinfecting apparatus.

6. A disinfecting system according to claim 5, further comprising:
    a fixed window defined in said one of said wall means and said door and which said handle is disposed;

a semicylindrical cover mounted to said one of said wall means and said door adjacent said window so as to be pivotable about a cylinder axis parallel to a longitudinal axis of said handle;

wherein said semicylindrical cover is placed in a first position that obstructs the window from inside said chamber when said apparatus is in said first state and said semicylindrical cover is placed in a second position that obstructs the window from outside said chamber when said apparatus is in said second state.

7. A disinfecting system according to claim 5, further comprising:

a fixed window defined in said one of said wall means and said door, wherein said handle is fixedly mounted so as to be within an interior of said chamber adjacent to the window;

a moveable plate mounted upon an inner surface of said one of said wall means and said door adjacent to said window, said plate closing said window by obstructing it in a first position and opening said window by not obstructing it in a second position;

wherein said moveable plate is placed into said second position when said disinfecting apparatus is placed into said first state and said moveable plate is placed into said first position when said disinfecting apparatus is placed into said second state.

8. A disinfecting system comprising:

a disinfecting apparatus comprising wall means defining a disinfection chamber, a door for providing selective access to said disinfection chamber, means for disinfecting objects placed within said chamber, and a handle mounted to one of said door and said wall means, wherein said handle is comprised of first and second portions;

wherein an improvement comprises:

handle disinfecting means for selectively, automatically disinfecting said handle while mounted to said disinfecting apparatus, said handle disinfecting means including means for moving said handle through a plane defined by said one of said wall means and door between a first and second position, wherein in said first position said first handle portion is within said disinfection chamber and said second handle portion is outside said disinfection chamber and in said second position said first handle portion is outside said disinfection chamber and said second handle portion is within said disinfection chamber; and control means for controlling an operation of said handle disinfecting means, said control means disposing said first or second handle portion into said chamber on the basis of a predetermined cleaning cycle of said disinfecting apparatus.

9. A disinfecting system according to claim 8 wherein:

the handle is a closed ring, half disposed within the disinfecting apparatus and half disposed outside of the disinfecting apparatus.

10. A disinfecting system comprising:

a disinfecting apparatus comprising wall means defining a disinfection chamber, a door for providing selective access to said disinfection chamber, and means for disinfecting objects placed within said chamber;

wherein an improvement comprises:

a first handle mounted on a first side of said door;

a second handle mounted on a second side of said door;

handle disinfecting means for selectively, automatically disinfecting one of said first and second handles while mounted to the door by exposing one of said first and second handles to the chamber of said disinfecting apparatus, said handle disinfecting means including hinge means for selectively reversing a facing disposition of said first and second sides of said door; and control means for controlling an operation of said handle disinfecting means, said control means controlling the operation of said hinge means so as to reverse the a facing direction of said first and second sides of said door on the basis of a predetermined cleaning cycle of the disinfecting apparatus.

* * * * *